(12) United States Patent
Shepherd et al.

(10) Patent No.: US 9,442,076 B2
(45) Date of Patent: Sep. 13, 2016

(54) INFRARED RADIOMETRIC IMAGING INSPECTION OF STEEL PARTS

(71) Applicant: Bell Helicopter Textron Inc., Fort Worth, TX (US)

(72) Inventors: Robert A. Shepherd, Fort Worth, TX (US); David R. Schlichte, Irving, TX (US); Catherine Ferrie, North Richland Hills, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 0 days.

(21) Appl. No.: 14/569,172

(22) Filed: Dec. 12, 2014

(65) Prior Publication Data

US 2016/0169813 A1 Jun. 16, 2016

(51) Int. Cl.
*G01N 21/88* (2006.01)
*G01N 21/95* (2006.01)

(52) U.S. Cl.
CPC ...... *G01N 21/8806* (2013.01); *G01N 21/9515* (2013.01); *G01N 2201/061* (2013.01)

(58) Field of Classification Search
CPC .................. G01N 21/9515; G01N 2201/061; G01N 21/8806
See application file for complete search history.

(56) References Cited

U.S. PATENT DOCUMENTS

| | | | |
|---|---|---|---|
| 2002/0160612 A1* | 10/2002 | Kobayashi | H01L 21/28123 438/694 |
| 2005/0221229 A1* | 10/2005 | Nasser-Ghodsi | G01N 1/32 430/296 |
| 2015/0001421 A1* | 1/2015 | Sappey | G01N 21/6489 250/459.1 |
| 2015/0193919 A1* | 7/2015 | Nissen | G01N 21/91 348/92 |

* cited by examiner

*Primary Examiner* — Yara B Green
(74) *Attorney, Agent, or Firm* — Fish & Richardson P.C.

(57) ABSTRACT

One example of a method includes heating a ground steel part that has been chemical-etched. The method also includes detecting defects caused by grinding and watermarks caused by chemical etching by imaging the steel part with an infrared camera to capture infrared radiation from regions of the steel part that include defects and watermarks. Imaging the steel part can include imaging regions of the steel part at long-wavelengths of infrared radiation to detect defects on the regions of the steel part and generating a first image wherein the defects are visible in the image and the watermarks are not visible in the image.

17 Claims, 5 Drawing Sheets

INFRARED RADIOMETRIC IMAGING INSPECTION OF STEEL PARTS

TECHNICAL FIELD

This disclosure relates to the inspection of parts, e.g., components of a machine.

BACKGROUND

Grinding is an important technique used in the manufacture of many parts, e.g., steel parts such as gears. However, the grinding process can introduce intense localized heating in the machined part, resulting in thermal damage often called "burns." The thermal damage creates defects and weakened regions in the part that can be prone to cracking. Identifying regions of thermal damage on machined parts is a safety concern.

SUMMARY

This disclosure describes technologies relating to inspecting metallic parts with infrared radiometric imaging.

In some aspects, a method includes heating a ground steel part that has been chemical-etched. The method also includes detecting defects caused by grinding and watermarks caused by chemical etching by imaging the steel part with an infrared camera to capture infrared radiation from regions of the steel part that include defects and watermarks.

This, and other aspects, can include one or more of the following features. Imaging the steel part can include imaging regions of the steel part at long-wavelengths of infrared radiation to detect defects on the regions of the steel part and generating a first image wherein the defects are visible in the image and the watermarks are not visible in the image. Long-wavelengths of infrared radiation can include wavelengths greater than or equal to 6 microns. Imaging the steel part can include imaging the regions of the steel part at mid-wavelengths of infrared radiation to detect defects and watermarks on the regions of the steel part and generating a second image wherein the defects and the watermarks are visible in the image. Mid-wavelengths of infrared radiation can include infrared wavelengths less than 6 microns. Imaging the steel part can include detecting infrared emittance from a region on the steel part that includes defects. Imaging the steel part can include detecting infrared reflectance from a region on the steel part that includes defects. A chemical etchant can be applied to a portion of the surface of the steel part. The chemical etchant can be a nital etch. The steel part can be a gear. Heating the steel part can include irradiating the steel part with a light source. Heating the steel part can include placing the steel part in thermal contact with a heated surface.

In some aspects, a method includes applying a chemical etchant to a surface of a steel part, exposing the steel part to a heat source, imaging the steel part with an infrared camera to generate an infrared image of a region of the steel part, and identifying defects on the region of the steel part.

This, and other aspects, can include one or more of the following features. The chemical etchant can be a nital etch. Heating the steel part can include irradiating the steel part with a light source. Defects can be visible in the infrared image of the region of the steel part. The steel part can be a gear.

In some aspects, a method includes applying a chemical etchant to a surface of a gear for a rotorcraft, heating the gear by exposing the gear to a heat source, imaging the heated gear with an infrared camera to generate an infrared image of a region of the gear, and identifying defects on the region of the gear.

This, and other aspects, can include one or more of the following features. The chemical etchant can be a nital etch. Defects can be visible in the infrared image of the region of the gear.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
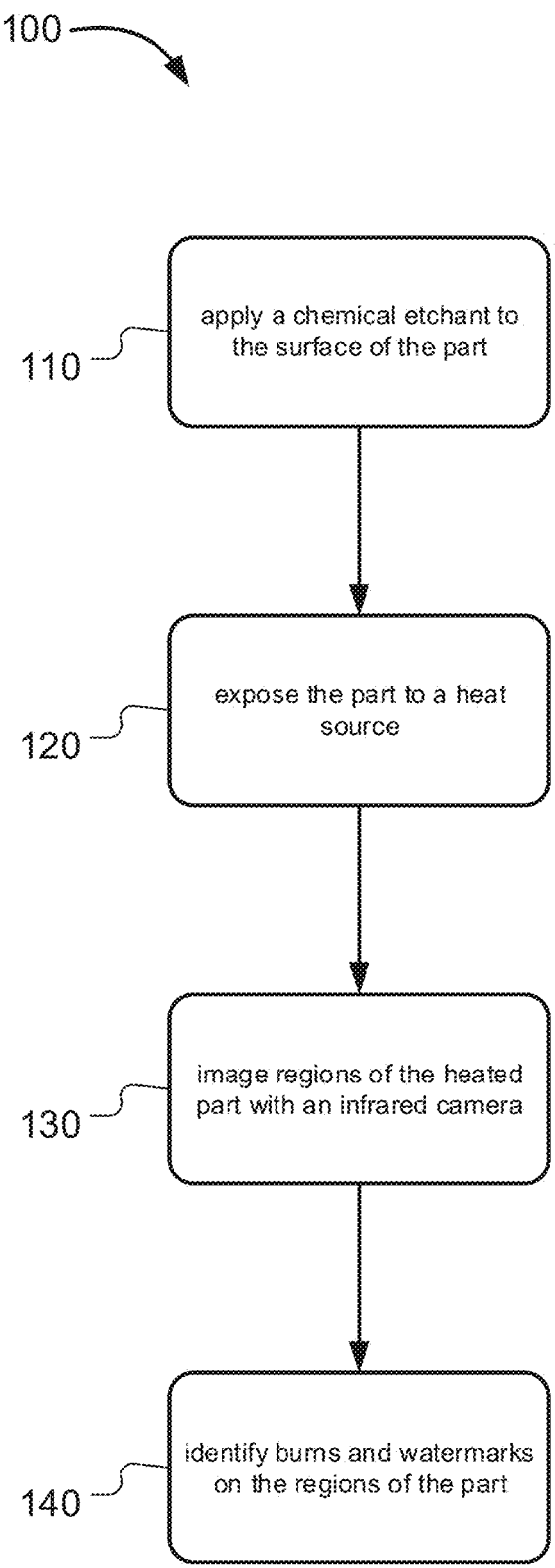
FIG. 1 is a flowchart showing an example process for inspecting a part.

This disclosure relates to the inspection of metallic parts using infrared radiometric imaging. During the manufacture of metallic parts, localized regions of the parts can experience high temperatures that cause thermal damage, resulting in damaged regions with defects called "burns." Any machining operation that produces friction or results in the part being heated and/or portions of the part being removed can cause defects. For example, a machining or grinding process can produce defects on the surface of the ground part. Defects can also be produced by directly heating the part, for example during a heat treatment of the part. The defects introduce regions of weakness relative to regions without the defects. Regions with the defect can be prone to cracking, breaking, or other failure. Thus, identification of defects on a part is an important safety consideration. Applying certain chemical etchants such as nital etch can delineate the defects, allowing visual identification of the burns. However, chemical etchants can also leave residual watermarks that are difficult to distinguish from discolored defects. An accepted part with a defect misidentified as a watermark could later fail during operation. Conversely, a part with a watermark misidentified as a defect could be unnecessarily rejected.

This disclosure describes a non-destructive process for inspecting a metallic part using infrared imaging. The metallic part can be made of a metal such as steel (e.g., a hardened carbon steel) or another metal. In an example implementation, a machined part is treated with chemicals such as those described below. The chemical treatment can identify defects, e.g., burns or other defects, on the surface of the machined part while also leaving residual watermarks on the surface. The chemically treated part is heated, and then the heated part is imaged at infrared wavelengths. The images are inspected to detect the defects caused by the machining and the watermarks caused by chemical etching. The defects and watermarks can be distinguished by their different characteristics apparent in the infrared image.

The techniques described here can be implemented to distinguish defects in machined parts from residual watermarks left by chemical treatment of the machined parts, ensuring that damaged parts are properly identified. The inspection process can be used to inspect any metallic part manufactured for any applicable industry, e.g., rotorcraft, aircraft, automobiles, and other industries. For example, the part could be a hardened steel gear or other transmission component. The inspection process can use multiple wavelengths of infrared radiation (e.g., mid-wavelength infrared, long-wavelength infrared) to inspect the part.

When examined in the visual spectrum (e.g. using the human eye), defects and residual watermarks can appear very similar and be mistaken for one another. Defects and residual watermarks can have different appearances and characteristics when inspected in infrared wavelengths, and thus burns can be distinguished from watermarks using infrared imaging. Furthermore, contrast between defects and undamaged regions can be enhanced using infrared cameras because infrared cameras are not as sensitive to microscopic surface features, films, or contaminates. For example, an infrared image can show greater contrast between defects or watermarks and the surrounding regions of the part. The inspection process allows digital reproduction of inspection images, and the inspection process is reproducible. The digital and reproducible nature of the inspection process can allow calibration of the infrared images to quantitatively determine infrared reflectivity and emissivity. The infrared images can be correlated to burn characteristics (e.g., burn depth, burn severity, etc.) with greater precision and reliability than a visual inspection of the burn. Furthermore, the digital and reproducible nature of the inspection process can allow a standardization and gradation of burn characteristics.

FIG. 1 shows an example infrared inspection process 100. The inspection process 100 can be used to inspect a machined, ground, or otherwise processed metallic part, e.g., a hardened steel part or other metallic part. For example, the part can be any metallic part manufactured by grinding such as a gear, shaft, spline, bearing, screw, rod, or other part. For example, the part can be a ground gear used in a rotorcraft transmission.

At 110 in the inspection process 100, a chemical etchant is applied to the surface of the part. The chemical etchant is an etchant that delineates (e.g. darkens, discolors) defects on the part. For example, the chemical etchant can be a nital etch, a picral etch, or some other etchant. The chemical etchant can be applied to a portion of the part or the entire part (e.g., by immersion in the etchant or other techniques). In some implementations, the part is rinsed and/or dried after application to remove the chemical etchant.

At 120, the chemical-etched part is heated by exposure to a heat source. For example, the part can be heated to a temperature greater than the ambient temperature (e.g., greater than room temperature). In some implementations, the entire part is heated to a temperature, and in some implementations, a portion of the part is heated to a temperature. The part can be heated by any suitable heat source, such as the light source 204 shown in FIG. 2A or the heat source 210 shown in FIG. 2B, or another heat source.

At 130, the heated part is imaged with an infrared camera. Imaging regions of the part in the infrared spectrum can detect defects on the part with greater contrast and reliability than imaging in the visible spectrum. For example, imaging regions of the part at long-wavelengths of infrared radiation can detect defects on the regions of the part. In particular, imaging a chemical-etched and heated part at long-wavelength infrared can generate an image in which defects are less visible in the image than watermarks. Additionally, imaging regions of the part at mid-wavelengths of infrared radiation can detect defects and watermarks on the regions of the part. In particular, imaging the part at mid-wavelength infrared can generate an image in which both defects and the watermarks are visible in the image.

At 140, defects and watermarks are identified based on the images of the part. For example, defects could be identified by their greater visibility in infrared images compared with watermarks and regions without defects. Conversely, watermarks could be identified by their reduced visibility in infrared images compared with defects.

Figure 2A:
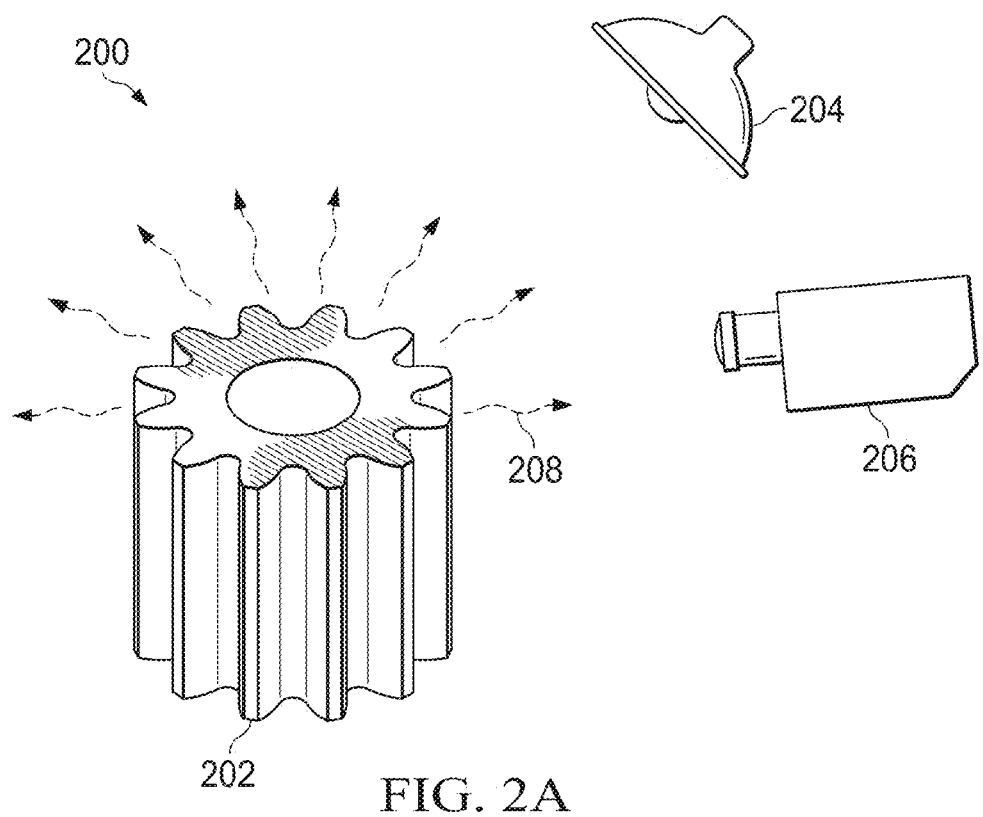
FIGS. 2A-2B are schematic diagrams showing examples of a system for inspecting a part.
Figure 2B:
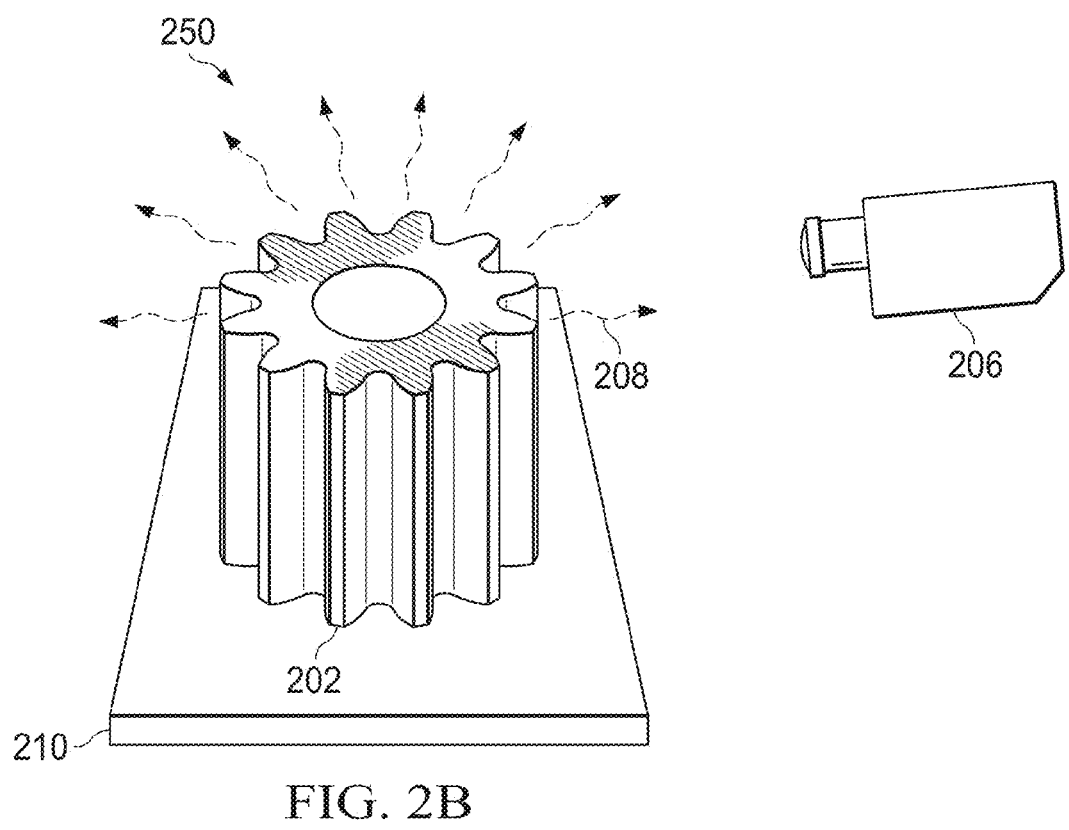

FIG. 2A and FIG. 2B illustrate schematic diagrams of example inspection systems 200 and 250, respectively. The example inspection systems 200, 250 can implement the inspection process 100. Each of the example inspection systems 200, 250 includes an example part 202 and an example infrared camera 206. In FIGS. 2A-B, the part 202 is shown as a ground gear that has been chemical-etched.

In some implementations, an inspection system 200 includes an example light source 204. The light source 204 irradiates the part 202. The part 202 absorbs the light emitted from light source 204, and as such, the light source 204 serves to heat the part 202. The light source 204 can be an incandescent lamp, a halogen lamp, a heat lamp, a laser, or another type of light source. The light source 204 can be positioned a distance away from the part 202, e.g. 3 inches away, 1 foot away, or another distance away. A portion of the part 202 or all of the part 202 can be irradiated by the light source 204. Multiple light sources can be used to irradiate multiple portions of the part 202. Optical components (e.g., lenses, mirrors, or other optical components) can be used to direct radiation from the light source 204 onto a portion of the part 202.

The infrared camera 206 can capture a portion of infrared radiation 208 from the part 202. For example, the infrared camera can be an FSI Phoenix MWIR FPA infrared camera, an FSI Phoenix LWIR FPA infrared camera, or another infrared camera. The infrared camera can also be implemented by an infrared detector such as an InSb infrared detector or an InGaAs infrared detector, or another type of infrared detector. In some implementations, the infrared camera 206 detects infrared radiation 208 as emittance from a heated part 202. In some implementations, the light source 204 irradiates the part 202, and the infrared camera 206 detects infrared radiation 208 as reflectance from the part 202. In some implementations, the light source 204 is turned off during detection of infrared radiation 208, and the infrared radiation 208 is detected as emittance from the part 202. In some implementations, the light source 204 is modulated, and the infrared camera 206 is connected to a lock-in amplifier to enhance detection of the infrared radiation 208. The infrared camera 206 is used to generate an image of one or more regions of the part 202 in an infrared spectrum. For example, the infrared camera 206 can capture infrared radiation and convert a portion of the captured infrared radiation into signals. The infrared camera 206 can transmit the signals to another device (e.g. a computer, a module, an amplifier, or another device) that can generate images from the signals. In some implementations, the infrared camera 206 captures long-wavelength infrared radiation (i.e., wavelengths greater than or equal to 6 microns). In some implementations, the infrared camera 206 captures mid-wavelength infrared radiation (i.e., infrared wavelengths between about 2 and 6 microns). In some implementations, multiple infrared cameras 206 are used. The multiple infrared cameras 206 can be configured to capture different infrared spectra. The infrared spectra can include different wavelengths or the same wavelengths. For example, one camera can capture mid-wavelength infrared radiation and another camera can capture long-wavelength infrared radiation.

Figure 3A:
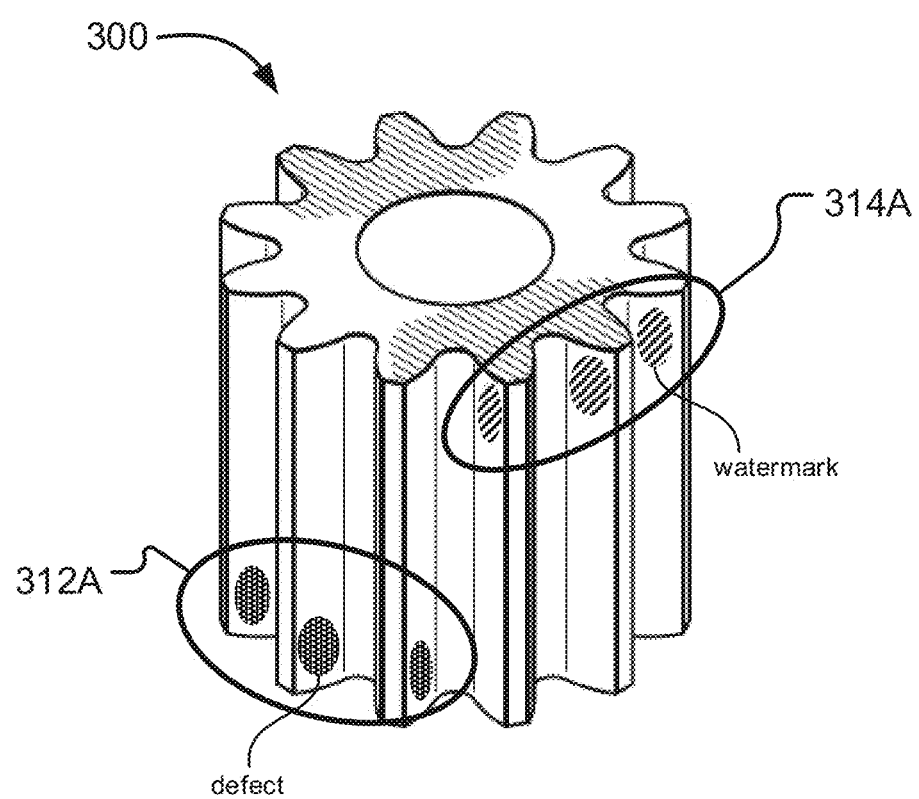
FIG. 3A is a schematic diagram of an example part inspection.

FIG. 3A shows a schematic diagram of an example part 300 as seen in the visible spectrum. The example part 300 has been ground and chemical-etched with nital etch. Representative defects are apparent on part 300 at region 312A. The defects in region 312A appear as dark spots on the surface of the part 300 (one example defect is labeled). The part 300 also shows representative watermarks in region 314A, the watermarks also appearing as dark spots (one example watermark is labeled). In FIG. 3A, the dark spots of the defects in region 312A are similar in appearance to the dark spots of the watermarks in region 314A, and each could possibly be misidentified as the other. FIG. 3A is representative of parts on which both defects and watermarks are apparent in the visual spectrum.

Figure 3B:
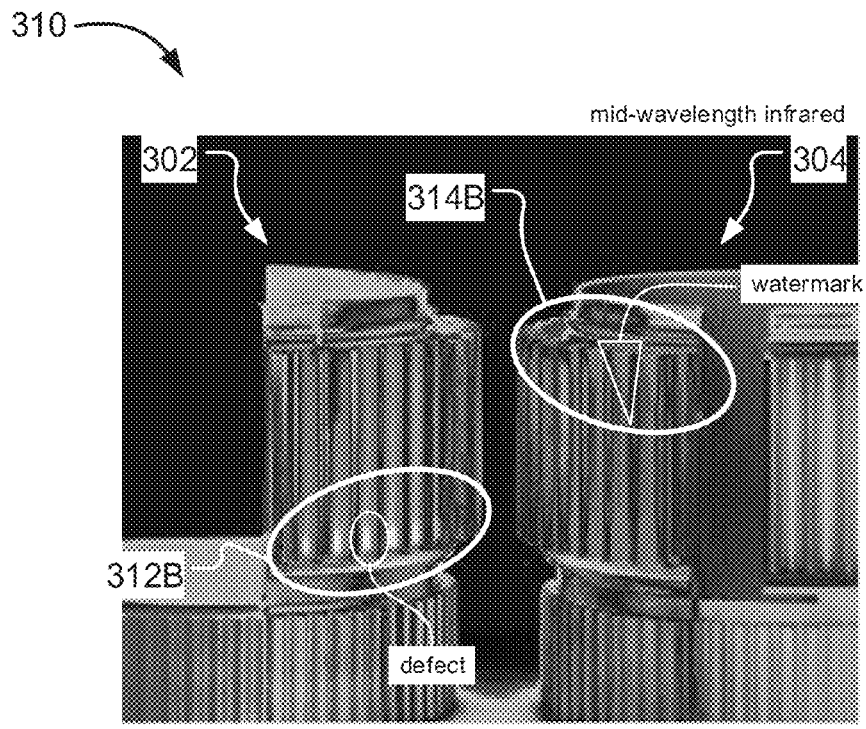
FIGS. 3B-3C are example images of a part inspection.

FIG. 3B shows an example image 310 of example parts 302 and 304 imaged with a mid-wavelength infrared camera. Parts 302 and 304 have been ground, chemical-etched with nital etch, and heated using a light source, similar to inspection system 200 implementing inspection process 100. Image 310 in FIG. 3B is an image of mid-wavelength infrared emittance from parts 302, 304. In FIG. 3B, stronger intensity (shown in false-color) corresponds to greater radiative emittance from the parts 302, 304. The mid-wavelength infrared image 310 shows defects present in region 312B as spots of stronger intensity (one example defect has been labeled). Watermarks are also apparent in region 314B as spots of higher intensity (one example watermark has been labeled). Imaging in mid-wavelength infrared can show burns and watermarks with greater clarity and greater conspicuity than imaging in the visible spectrum.

Figure 3C:
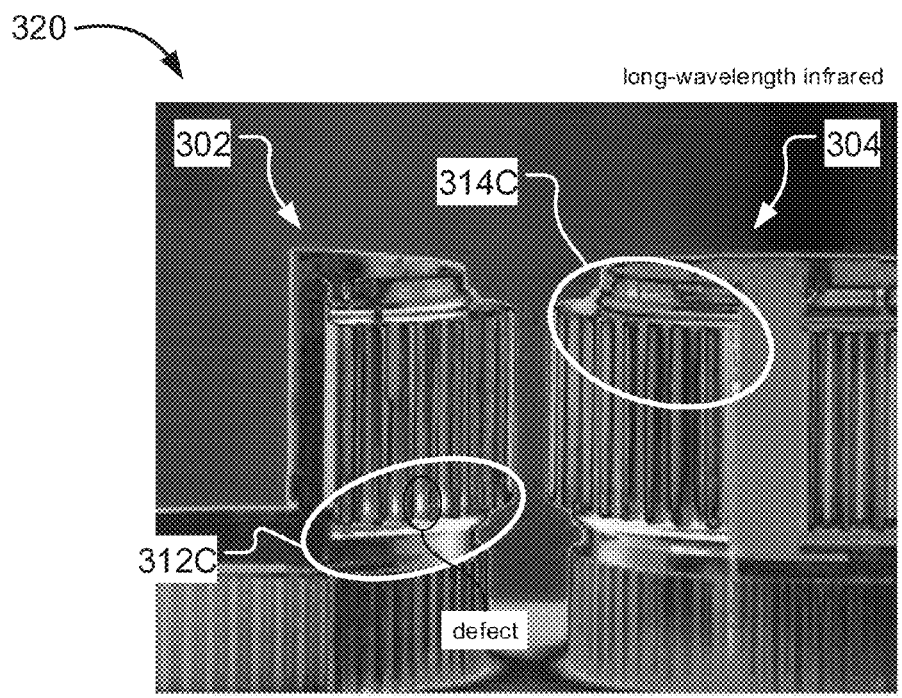

FIG. 3C shows an example image 320 of parts 302 and 304 imaged with a long-wavelength infrared camera. Image 320 in FIG. 3C is an image of long-wavelength infrared emittance from parts 302, 304. In FIG. 3C, stronger intensity (shown in false-color) corresponds to greater radiative emittance from the parts 302, 304. The parts 302, 304 are the same parts as in FIG. 3B, and regions 312C, 314C in FIG. 3C are the same regions on parts 302, 304 as regions 312B, 314B shown in FIG. 3B. Defects are apparent in FIG. 3C as spots of stronger long-wavelength infrared intensity in region 312C (one example defect has been labeled). However, watermarks are not apparent in region 314C in the long-wavelength infrared image of FIG. 3C.

The defects on parts can be positively identified or verified by their long-wavelength infrared emission, and the watermarks on parts can be positively identified or verified by relatively weak long-wavelength emission or their lack of long-wavelength infrared emission. In some cases, the watermarks can be positively identified by their weaker long-wavelength infrared emission relative to the long-wavelength infrared emission from defects. In this manner, infrared inspection of parts in a process such as process 100 can identify and distinguish defects and watermarks more reliably than visible spectrum inspection.

In some implementations, an inspection system 250 includes an example heat source 210 that heats the part 202. In FIG. 2B, the heat source 210 is shown as a heated surface (e.g., a hot plate) that is proximate to or in contact with the part 202. The part 202 can rest on the heat source 210 or can be heated by the heated surface 210 through an intermediate material (not shown) or be near but not in physical contact with the heat source 210. In some implementations, another type of heat source is used, such as hot gas convection (e.g., via a heat gun, a hair dryer, or other hot gas supply), a flame, a furnace, a space heater, or other heat source. In some implementations, multiple heat sources of the same type or of different types are used to heat the part 202. The inspection system 250 could be used to generate images similar to images 300, 310, 320 shown in FIGS. 3A-3C. For example, the parts 302, 304 could be heated with a hot plate instead of with a light source. In some implementations, the heat source 210 is turned off during detection of infrared radiation 208. In some implementations, the part 202 is removed from proximity to the heat source 210 prior to detection of the infrared radiation 208. In some implementations, the heat source 210 is modulated, and the infrared camera 206 is connected to a lock-in amplifier to enhance detection of the infrared radiation 208.

Figure 4:
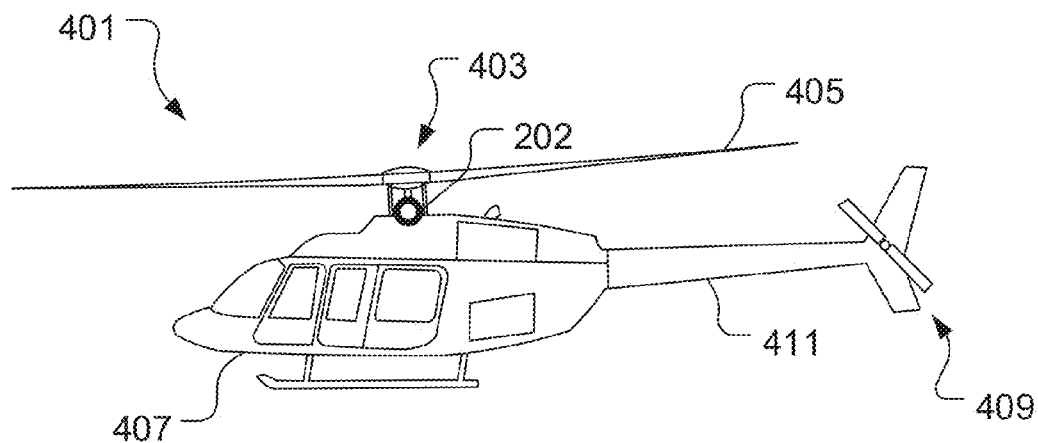
FIG. 4 is a schematic diagram showing an example of a rotorcraft.

The inspection process 100 can be used to inspect parts for an aircraft. As an example, FIG. 4 shows a schematic diagram of an example rotorcraft 401. Rotorcraft 401 has a rotor system 403 with multiple rotor blades 405. Rotorcraft 401 can further include a fuselage 407, anti-torque system 409, and an empennage 411. The rotorcraft 401 can also include parts 202 that can be inspected by inspection process 100. Part 202 is shown in an example location within the transmission of the rotorcraft 401.

Figure 5:
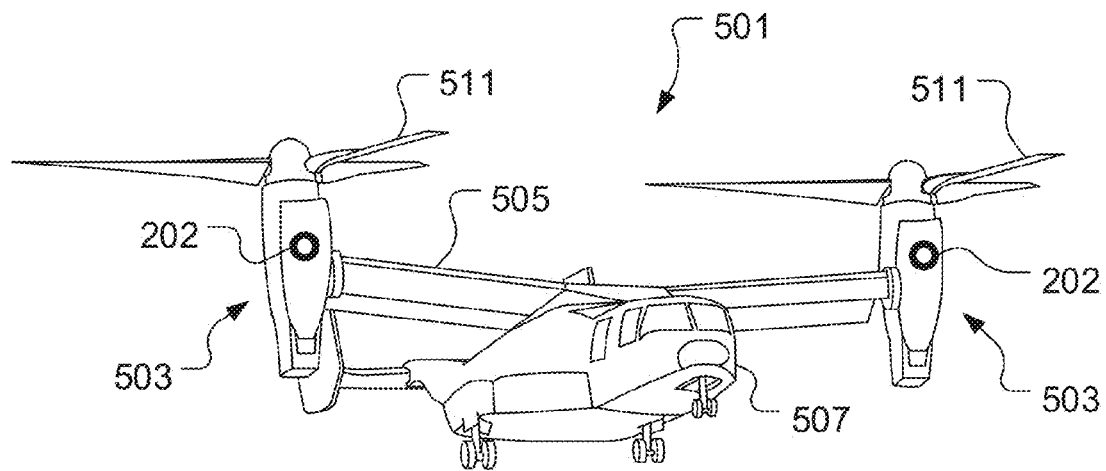
FIG. 5 is a schematic diagram showing an example of a tiltrotor aircraft.

As another example aircraft, FIG. 5 shows a schematic diagram of an example tiltrotor aircraft 501. Aircraft 501 includes a fuselage 507 with attached wings 505. Nacelles 503 are carried at the outboard ends of wings 505 and are rotatable between the helicopter-mode position shown and a forward-facing airplane-mode position (not shown). Nacelles 503 carry engines and transmissions for powering rotor systems 511 in rotation. An engine may be an internal combustion engine, an electrical power source and associated motor, or any other suitable technique for powering rotor system 511. The tiltrotor aircraft 501 can include parts 202 that can be inspected by inspection process 100. Part 202 is shown in an example location within the transmission of the tiltrotor aircraft 501.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results

What is claimed is:
1. A method comprising:
heating a ground steel part that has been chemical-etched; and
detecting defects caused by grinding and watermarks caused by chemical etching by imaging the steel part with an infrared camera to capture infrared radiation from regions of the steel part that include defects and watermarks, wherein imaging the steel part comprises:
imaging regions of the steel part at long-wavelengths of infrared radiation to detect defects on the regions of the steel part; and
generating a first image wherein the defects are visible in the image and the watermarks are not visible in the image.

2. The method of claim 1, wherein long-wavelengths of infrared radiation comprise wavelengths greater than or equal to 6 microns.

3. The method of claim 1, wherein imaging the steel part further comprises:
   imaging the regions of the steel part at mid-wavelengths of infrared radiation to detect defects and watermarks on the regions of the steel part; and
   generating a second image wherein the defects and the watermarks are visible in the image.

4. The method of claim 3, wherein mid-wavelengths of infrared radiation comprise infrared wavelengths less than 6 microns.

5. The method of claim 1, wherein imaging the steel part comprises detecting infrared emittance from a region on the steel part that includes defects.

6. The method of claim 1, wherein imaging the steel part comprises detecting infrared reflectance from a region on the steel part that includes defects.

7. The method of claim 1, wherein a chemical etchant has been applied to a portion of the surface of the steel part.

8. The method of claim 7, wherein the chemical etchant is a nital etch.

9. The method of claim 1, wherein the steel part is a gear.

10. The method of claim 1, wherein heating the steel part comprises irradiating the steel part with a light source.

11. The method of claim 1, wherein heating the steel part comprises placing the steel part in thermal contact with a heated surface.

12. A method comprising:
   applying a chemical etchant to a surface of a steel part;
   exposing the steel part to a heat source;
   imaging the steel part with an infrared camera to generate an infrared image of a region of the steel part at long-wavelengths of infrared radiation; and
   identifying defects on the region of the steel part by generating a first image responsive to the imaging, wherein the defects are visible in the image and watermarks are not visible in the image.

13. The method of claim 12, wherein the chemical etchant is nital etch.

14. The method of claim 12, wherein heating the steel part comprises irradiating the steel part with a light source.

15. The method of claim 12, wherein the steel part is a gear.

16. A method comprising:
   applying a chemical etchant to a surface of a gear for a rotorcraft;
   heating the gear by exposing the gear to a heat source;
   imaging the heated gear with an infrared camera to generate an infrared image of a region of the gear at long-wavelengths of infrared radiation; and
   identifying defects on the region of the gear by generating a first image wherein the defects are visible in the image and watermarks are not visible in the image.

17. The method of claim 16, wherein the chemical etchant is nital etch.

* * * * *